United States Patent
Jasinschi et al.

(10) Patent No.: US 10,539,640 B2
(45) Date of Patent: Jan. 21, 2020

(54) MRI PROTOCOL FOR SEGMENTATION OF AN IMAGE DETAIL USING IMAGES ACQUIRED AT TWO DIFFERENT MAGNETIC FIELD STRENGTHS

(71) Applicant: KONINKLIJKE PHILIPS N.V., Eindhoven (NL)

(72) Inventors: Radu Serban Jasinschi, Eindhoven (NL); Rudolf Mathias Johannes Nicolaas Lamerichs, Eindhoven (NL); Peter Boernert, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 353 days.

(21) Appl. No.: 15/521,643

(22) PCT Filed: Oct. 30, 2015

(86) PCT No.: PCT/EP2015/075322
§ 371 (c)(1),
(2) Date: Apr. 25, 2017

(87) PCT Pub. No.: WO2016/066826
PCT Pub. Date: May 6, 2016

(65) Prior Publication Data
US 2017/0248669 A1 Aug. 31, 2017

(30) Foreign Application Priority Data
Oct. 31, 2014 (EP) .................................... 14191230

(51) Int. Cl.
*G01R 33/56* (2006.01)
*G01R 33/44* (2006.01)
(Continued)

(52) U.S. Cl.
CPC .......... *G01R 33/5608* (2013.01); *A61B 5/055* (2013.01); *G01R 33/445* (2013.01); *G01R 33/5611* (2013.01); *G01R 33/5617* (2013.01)

(58) Field of Classification Search
CPC .... G01R 33/56; G01R 33/5608; G01R 33/44; G01R 33/445; G01R 33/561;
(Continued)

(56) References Cited

U.S. PATENT DOCUMENTS 6,490,472 B1 12/2002 Li et al.
2008/0103383 A1 5/2008 Van Der Kouwe et al.
(Continued)

OTHER PUBLICATIONS

G. Frisoni et al Mapping Local Hippocampal Changes in Alzheimer's Disease and Normal Ageing with MRI at 3 Tesla, Brain (2008) vol. 131, p. 3266-3276.
(Continued)

*Primary Examiner* — Son T Le

(57) ABSTRACT

A magnetic resonance imaging protocol includes an acquisition segment to control an acquisition sequence to acquire magnetic resonance signals at a lower main magnetic field strength. A reconstruction segment controls reconstruction of a diagnostic magnetic resonance image from the magnetic resonance signals at a lower main magnetic field strength. A segmentation segment controls segmentation of a predetermined image detail of the diagnostic magnetic resonance image. In the magnetic resonance imaging protocol, the acquisition sequence has a set of imaging parameters that cause the image quality of the diagnostic magnetic resonance to be similar to the image quality of the magnetic resonance training images, e.g., acquired at 7 T. The segmentation segment includes an initialization portion which controls (i) access to a set of magnetic resonance training images acquired at main magnetic field of a higher main magnetic field strength (ii) registration of the diagnostic magnetic resonance image to one or more of the magnetic resonance training images and (iii) a segmentation proper applied to the diagnostic image to segment the predetermined detail from the registered diagnostic magnetic resonance image.

16 Claims, 3 Drawing Sheets

(51) Int. Cl.
*A61B 5/055* (2006.01)
*G01R 33/561* (2006.01)

(58) Field of Classification Search
CPC ............... G01R 33/5617; G01R 33/54; G01R 33/5611; A61B 5/055
See application file for complete search history.

(56) References Cited

U.S. PATENT DOCUMENTS

2010/0016706 A1 1/2010 Wohlgemuth
2015/0168526 A1* 6/2015 Kang ................ G01R 33/5615
324/309

OTHER PUBLICATIONS

M Fotuhi, D Do, and C. Jack, Modifiable factors that alter the size of the hippocampus, Nature Reviews Neurology, 8, 189-202, 2012.
G. Kerchner et al "Hippocampal Neuropil Atrophy in Early Alzheimer's Disease" Alzheimers&Dementia, Jul. 2010 vol. 6, Issue 4.
K. MacDonald "Automated Template-Based Hippocampal Segmentations from MRI: the effects of 1.5T" Neuroinform Jan. 7, 2014.
G. Kerchner "Ultra-High Field 7T MRI: A New Tool for Studying Alzheimer's Disease" Journal of Alzheimer's Disease, 26 (2011) p. 91-95.
G. Winston et al "Automated Hippocampal Segmentation in Patients with Epilepsy" Epilepsia, vol. 54, No. 12, p. 2166-2173.
Papoutsaki et al "Polymer Gel Dosimetry Utilizing a 2D (SE) and a 2D (HASTE) Multiple Echo Sequences"Journal of Physics, vol. 444, Jul. 26, 2013 p. 12088.
Kahn et al "Optimal Weights for Local Multi-Atlas Fusion Using Supervised Learning and Dynamic Information .." Neuroimage, vol. 56, No. 1, Jan. 28, 2011 p. 126-139.
Patel et al "Half-Fourier Acquisition Single Shot Turbo Spin-Echo.." American Journal of Neuroradiology, vol. 18, No. 9, Oct. 1, 1997 p. 1635-1640.

* cited by examiner

MRI PROTOCOL FOR SEGMENTATION OF AN IMAGE DETAIL USING IMAGES ACQUIRED AT TWO DIFFERENT MAGNETIC FIELD STRENGTHS

CROSS REFERENCE TO RELATED APPLICATIONS

This application is a U.S. national phase application of International Application No. PCT/EP2015/075322, filed on Oct. 30, 2015, which claims the benefit of EP Patent Application Serial No. 14191230.3 filed on Oct. 31, 2014 and is incorporated herein by reference.

FIELD OF THE INVENTION

The invention pertains to a magnetic resonance imaging protocol for segmentation of an image detail.

BACKGROUND OF THE INVENTION

Such a magnetic resonance imaging protocol is known from the paper 'Automated template-based hippocampal segmentations from MRI: the effects of 1.5 T or 3 T fields strength on accuracy' by Kate E. Macdonald et al. in Neuroinform. (published on-line on 7 Jan. 2014).

Magnetic imaging protocols in this paper involve acquisition of magnetic resonance signals at different main magnetic field strengths of 1.5 T and 3.0 T. Further, this paper recognises that hippocampal volumetric measures may be useful for Alzheimer's Disease (AD) diagnoses and disease tracking. Because manual segmentation of the hippocampus from magnetic resonance images is labour-intensive, automated segmentation is needed for clinical use. To study its reliability, an automated hippocampal segmentation using hippocampal multi-atlas propagation and segmentation is applied to magnetic resonance images acquired at 1.5 T and are 3 T. Notably, it was investigated whether the automated segmentation is as accurate on 3 T scans as on 1.5 T scans.

SUMMARY OF THE INVENTION

An object of the invention is to provide a magnetic resonance imaging protocol that more accurately segments pre-determined image details, in particular the hippocampus from surrounding brain structure, from a magnetic resonance image.

This object is achieved according to the invention by the magnetic resonance imaging protocol an acquisition segment to control an acquisition sequence to acquire magnetic resonance signals at a lower main magnetic field strength, a reconstruction segment to control reconstruction of a diagnostic magnetic resonance image from the magnetic resonance signals at a lower main magnetic field strength and
a segmentation segment to control segmentation of a pre-determined image-detail of the diagnostic magnetic resonance image,
in which magnetic resonance imaging protocol:
the acquisition sequence has a set of imaging parameters that cause the image quality of the diagnostic magnetic resonance to be similar to the image quality of the magnetic resonance training images and
the segmentation segment comprises
an initialisation portion which controls
access to a set of magnetic resonance training images acquired at main magnetic field of a higher main magnetic field strength,
registration of the diagnostic magnetic resonance image to one or more of the magnetic resonance training images,
the one or more magnetic resonance training images including an image detail corresponding to the pre-determined image detail in the diagnostic magnetic resonance image and a segmentation proper applied to the diagnostic image to segment the pre-determined detail from the registered diagnostic magnetic resonance image.

The invention is based on the insight that the training images that were acquired at higher main magnetic field strength, notably at 7 T, often have a better spatial resolution and a better contrast resolution in which image details are better delineated than in the diagnostic images acquired at a lower main magnetic field strength, notably 3 T or 1.5 T. Thus, the image information of an image detail in the training images assists to improve the reliability of the segmentation of a corresponding image detail in the diagnostic image. Training images from several atlases of training image can be used. Thus, in the framework of the present invention, higher main magnetic field strength may represent ultra-high magnetic field (7 T and higher), while lower main magnetic field strength may indicate high magnetic field strength of 3 T, or a commonly used magnetic field strength of 1.5 T. The magnetic resonance imaging protocol of the invention may be formed as a method that has groups of methods steps for acquisition of magnetic resonance signal, groups of method steps for reconstruction of one or more magnetic resonance images from the magnetic resonance signal and groups of method steps for segmentation of a detail, such as substructure within an an organ of interest, from the magnetic resonance images and further groups of method steps may be included form image processing such as image registration steps. In practice the magnetic resonance imaging protocol may be implemented in software, i.e. in the form of a computer programme that has groups of instructions to run the groups of method steps of the magnetic resonance imaging protocol of the invention. The groups of instructions or method steps that each form a partial set of instructions for the magnetic resonance imaging protocol of the invention form segments, such as acquisition segments, reconstruction segments and segmentation segments that each contain groups of method steps or instructions that pertain to the groups of activities, acquisition, reconstruction and image processing such as segmentation and registration of the magnetic resonance imaging protocol of the invention. These segments each relate to a consistent part of the magnetic resonance imaging protocol each with distinct input and output. The output of one segment may in general from input for a next segment.

The concept of image detail concerns a pre-defined part of the magnetic resonance image that lends itself to be segmented from its surrounding in the magnetic resonance image. In particular, the image detail may relate to substructures within a part of the patient's anatomy that has structural or functional coherence, such an organ in the patient's anatomy or even a substructure of an organ. In particular, the present invention is applied substructures of the hippocampus in magnetic resonance imaging in neurology, so that the hippocampus' substructures form the image details. That is, the image details at a level of internal structures of an organ, notably a of brain structure part, such as the hippocampus.

The registration of the diagnostic magnetic resonance image, that is acquired at the lower magnetic field strength, relate to one or more of the magnetic resonance training images acquired at the higher field strength. The set of magnetic resonance training image may from an atlas of magnetic resonance training images and the diagnostic magnetic resonance image may be registered to one or more of the magnetic resonance training images from the atlas, to assess the most resembling magnetic resonance training images from the atlas. The atlas may collect magnetic resonance training images from a variety of training objects, notably of the brains of a number of healthy subjects. The registration is applied to magnetic resonance training images that contain the corresponding image details that is of interest in the diagnostic magnetic resonance image. For example, the training magnetic resonance image(s) to which the diagnostic magnetic resonance image is registered both represent the image detail of the hippocampus, or another organ and its substructures of interest.

The segmentation part, i.e. the segmentation segment in the magnetic resonance imaging protocol of the invention distinguishes an initialisation portions which includes steps or instructions prepare for the actual segmenting-out of the image detail. These initialisation steps in preparation of the actual segmenting-out relate to accessing the training magnetic resonance images, and registering the diagnostic magnetic resonance image to one or more of the training magnetic resonance images. The segmentation proper includes the instructions to segment-out the image details from the registered diagnostic magnetic resonance image.

A further insight of the invention is to adapt the magnetic resonance protocol, notably the acquisition sequence that is applied at lower main magnetic field strength to yield image data that resemble image data acquired at the higher main magnetic field strength. In the framework of this invention the term magnetic resonance protocol encompasses the combination of a magnetic resonance acquisition sequence, reconstruction of the magnetic resonance image, post-processing of the reconstructed image as well as signal processing to the acquired magnetic resonance signals.

This resemblance typically relates to signal-to-noise ratio SNR, image contrast between e.g. white matter (WM), grey matter (GM), and the cerebro-spinal fluid (CSF), and image details within each tissue type. Image contrast can be described quantitatively by image intensity histograms, e.g., distance between the three (GM, WM, CSF) peaks and the histogram overlap. In segmentation of the hippocampus, an important image detail is the thin dark region on $T_2$-weighted images that separates the CA1-region from the DG-region. It has to be visible also in the diagnostic images as a test of "similar" image quality. More concretely, similarity of image quality may involve (i) same spatial resolution, same T2-weighted contrast, similar distinction in the image between grey matter (GM), white matter (WM) and cerebro-spinal fluid (CSF), similar signal-to-noise rations of the images and similar scan time. Similar distinction between tissues, such as GM, WM and CSF amounts to less than 30% difference in contrasts between these tissues in the respective images. Similar signal-to-noise amounts of a difference between signal-to-noise values of less than 20% between the respective images. Similar scan time would amount to less than 30% difference in scan time, i.e. acquisition time of the magnetic resonance signal for the respective images.

The invention enables that, apart from the acquisition of the set of training images, the acquisition of the diagnostic image is acquired at the lower main magnetic field strength. The segmentation is model-based using information from the training images that leads to accurate segmentation results of the image detail from the diagnostic image without the need for magnetic resonance image acquisition for the diagnostic image at ultra-high main magnetic field strength. The model-based segmentation using the training images benefits from the higher spatial resolution in the training images that is due to the higher signal-to-noise ratio and higher spatial-resolution of the training images, which is a result from the higher magnetisation and shorter data acquisition time (the data acquisition time is similar for the training and diagnostic, e.g., 10 mins.) at the higher main magnetic field strength at e.g. 7 T. For example the training set is actually a set of atlases.

The model-based segmentation makes use of an atlas of the training magnetic resonance images. A global registration of the training magnetic resonance images is made to the diagnostic magnetic resonance image. The training magnetic resonance image is registered to the diagnostic magnetic resonance image. Thus, the highest image quality viz. that of the training image, is maintained for the diagnostic images; registration most often reduces image quality e.g. because of image interpolation artefacts. A volume-of-interest (VOI) is selected around the image detail, e.g. the hippocampus, from the registered diagnostic image and the corresponding volume of interested is also selected from the training magnetic resonance image(s). For example, on each hemisphere of the brain, i.e., there are two volumes-of-interest VOIs (left, right hemispheres) per brain volume. Then the volume-of-interest in the training magnetic resonance images is registered with respect to the corresponding volume-of-interest in the diagnostic magnetic resonance image. The selected volume of interest in the diagnostic image and the corresponding volume of interest in the training image pertain to regions around the corresponding image details, such as e.g. the hippocampus, in the diagnostic magnetic resonance image and in the training magnetic resonance image. On the basis of the registered volume-of-interest, the surface of the image detail (e.g. the surface of the hippocampus) is aligned with the corresponding image detail in the training magnetic resonance images. The segmentation proper is applied e.g. employing an energy minimisation, which is known per se in the field of image segmentation, to the aligned image detail. In fact, the image detail being more clearly represented in the training image assists in aligning the image detail in the diagnostic magnetic resonance image so that the segmentation proper is so well initialised that the image detail is accurately segmented, even if it is less well represented in the diagnostic magnetic resonance image. In this way the segmentation of the image detail from the diagnostic image benefits from the better image quality of the training magnetic resonance image, without the need for higher main magnetic field strength for the acquisition of the diagnostic magnetic resonance image. Notably, the magnetic resonance training magnetic resonance images are acquired at a high magnetic field strength at 7 T and its level of detail facilitates the accurate segmentation of notably the hippocampus from diagnostic magnetic resonance images at lower field strength of 3 T.

These and other aspects of the invention will be further elaborated with reference to the embodiments defined in the dependent Claims.

In a preferred implementation of the magnetic resonance imaging protocol of the invention the acquisition sequence is a 3D multi-echo single shot turbo-spin echo sequence in which:

the repetition time TR is in the range of 2000-3000 ms, preferably 2400 ms or 2200 ms, the echo time is in the range of 200-250 ms, preferably 211 ms or 226 ms, the echo train length has 150-170 echoes and echo spacing per shot in the range of 4.4/720 ms to 5.2/880 ms, preferably 4.8/804 ms and
which acquisition sequence performs a half-Fourier scanning of k-space in the phase-encode direction with a half-Fourier factor in the range of 0.60 to 0.73, preferably 0.675.

The echo train length is specified in terms of echo-spacing/echo train length, so that according to the invention the echo-spacing is in the range of 4.4-5.2 ms and the echo training length is in the range of 720-880 ms.
These parameters of the acquisition sequence achieve, when applied at the main magnetic field strength of 3 T, that the reconstructed magnetic resonance image that is reconstructed from the acquired magnetic resonance signal resembles an magnetic resonance image at a higher magnetic field strength of e.g. 7 T of the same anatomy. Thus, the diagnostic magnetic resonance images are acquired such that they resemble the training magnetic resonance images. Thus, in the diagnostic magnetic resonance image (based on data acquired at the lower main magnetic field strength of e.g. 3 T) the way image details are represented is closely to the way such image details are represented in the training images (based on data acquired at the higher main magnetic field strength of e.g. 7 T). This leads to good results in accurate segmentation of the image detail from the diagnostic magnetic resonance image supported by the use of the training magnetic resonance image.

The echo-train length (ETL) and the parallel imaging (PI) (e.g. SENSE) reduction factor is a compromise between short echo train length which reduces signal loss due to decay of the signal along the echo-train and loss of signal-to-noise ratio, due to the undersampling of k-space at higher parallel imaging reduction facto, at higher parallel imaging (PI) reduction factor. As usual, this reduction factor represents the degree of undersampling in k-space of the magnetic resonance signal relative the sampling density that satisfies the Nyquist criterion to avoid signal aliasing. The short echo train length renders the acquisition sequence less sensitive to motion (e.g. cardiac motion or respiratory motion) in the part of the patient to be examined to be examined. Good results are achieved by a modest undersampling along the first phase encode direction (e.g. reduction factor of 1.4) and a higher reduction for the second phase encode direction (e.g. reduction factor of 2.0). The first and second phase encoding direction are mutually orthogonal in k-space. Furthermore the ETL and echo-time are controlled by half-Fourier. Therefore, the optimal setting according to this aspect of the invention is a compromise of both SENSE and half-Fourier, resulting in the optimum echo-time and ETL. Notably, the choice of the echo time $T_E$ and the repetition time TR achieve a sufficient SNR of the acquired magnetic resonance signal, even such that only a single signal average (NSA=1) is sufficient. This limits the total signal acquisition time.

The magnetic imaging protocol of the invention has as a technical effect that it achieves a balance between sufficiently fine spatial resolution and sufficient tissue contrast. In alternative technical terms, k-space sampling distribution balances spatial resolution versus $T_2$-weighted contrast which appears to correspond to a delicate balance that is needed for successful segmentation of the hippocampus and its substructures. It is found that the usual standard magnetic resonance image sequences that are installed by the manufactures on commercial magnetic resonance examination systems are not sufficient to achieve this delicate balance.

The magnetic resonance imaging protocol of the invention has a signal acquisition which generates multiple spin echoes for each (single) shot to acquire one line in k-space (jn a Cartesian e.g. EPI, k-space trajectory.

Moreover, the acquisition sequence achieves an acquisition time of less than 10 mins. There is no need to administer contrast agents.

The invention achieves good results in segmentation of the hippocampus form diagnostic images of the patient's brain, notably hippocampus sub-structures, e.g., CA1, CA2, CA3, DG. The invention enables diagnosis, treatment monitoring and follow-up of Alzheimer's Disease (AD) without the need of magnetic resonance imaging at ultra-high field, apart from the generation of the set of training magnetic resonance image. The set of training magnetic resonance images can be used repeatedly for the segmentation of the hippocampus of several diagnostic magnetic resonance images. Notably, this segmentation allows detection of early atrophy in the hippocampus which appears to be an early indication for the onset of Alzheimer's disease. The combination according to the invention of ultra-high field strength atlases of the hippocampus sub-structures with the use of similar quality images at high-field strength consequently achieves a technical image processing result that enables the differential focal atrophy analysis, especially on longitudinal datasets. The invention may be employed in early diagnosis, screening of population or particular risk groups for Alzheimer's disease. The invention can be expanded also in the diagnosis and treatment follow-up of patients with post-traumatic stress disorder—PTSD—or for pre-operative selection of the dentate gyrus—DG—via our method in the ablation of the DG in temporal lobe epilepsy.

These and other aspects of the invention will be elucidated with reference to the embodiments described hereinafter and with reference to the accompanying drawing wherein

DETAILED DESCRIPTION OF THE EMBODIMENTS

Figure 1:
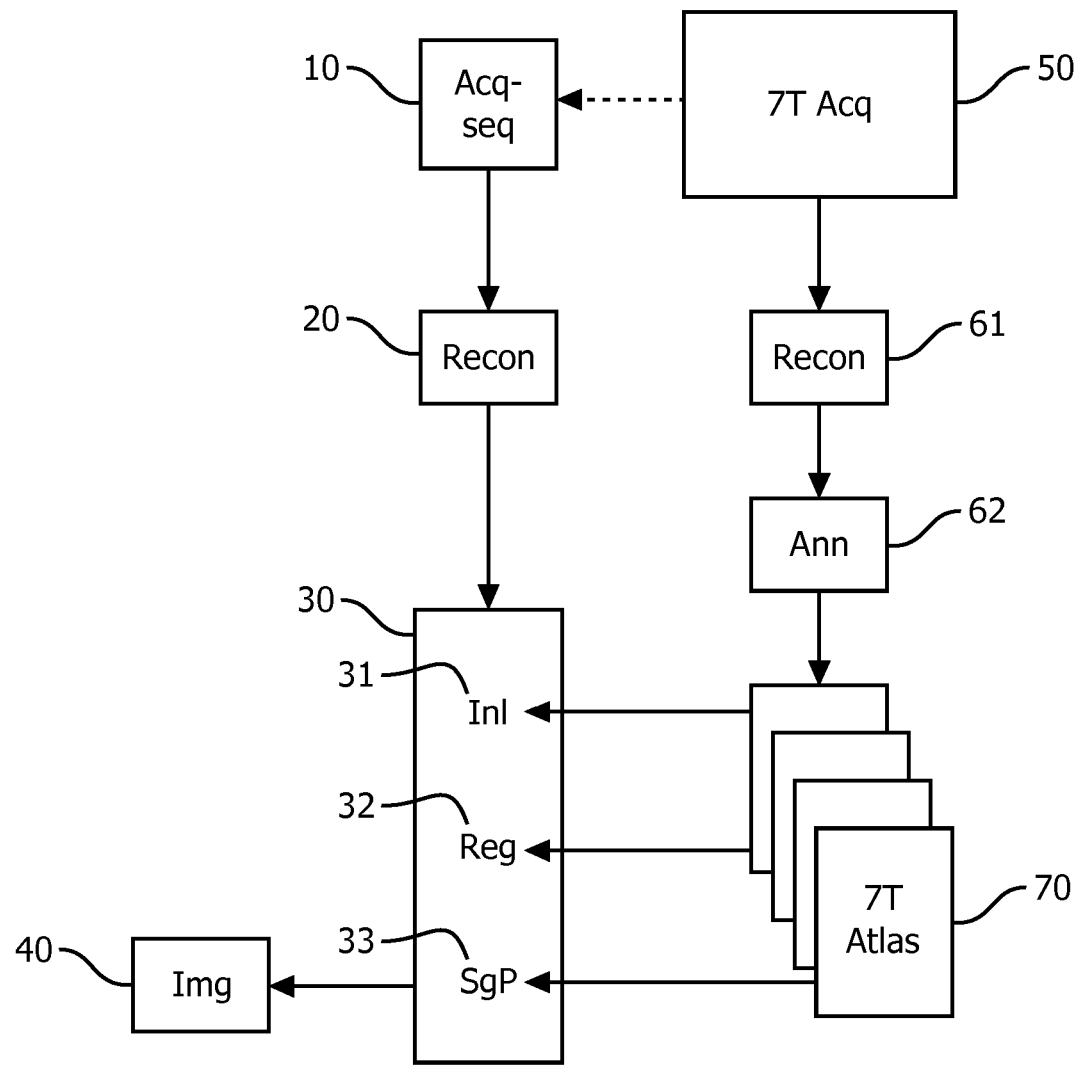
FIG. 1 shows a schematic representation of a magnetic resonance imaging protocol of the invention.

FIG. 1 shows a schematic representation of a magnetic resonance imaging protocol of the invention. The magnetic resonance signals for the diagnostic magnetic resonance imaging method are acquired in the acquisition segment 10 which is formed by a MR acquisition sequence that is translated from the MR acquisition sequence that is employed to generate the training magnetic resonance images from magnetic resonance signal acquired at a higher main magnetic field strength as compared to the field strength at which the magnetic resonance signals for the diagnostic image are acquired. The translation of the MR acquisition sequence at ultra-high (e.g. 7 T) to high (e.g. 3 T) or medium (1.5 T) field strengths achieves that the acquired magnetic resonance signal give rise to a similar image contrast in both the diagnostic and training magnetic resonance images. By way of a reconstruction segment 20, the diagnostic magnetic resonance image is reconstructed from the acquired magnetic resonance signal from the acquisition segment 10. This reconstruction is known per se e.g. in the form of in (inverse) fast Fourier transform. This reconstructed diagnostic magnetic resonance image is input into the segmentation segment 30. The segmentation segment 30 includes various stages. First an initialisation stage 31 is applied in which first a global registration of a training magnetic resonance image is made to the diagnostic image, after which the volume-of-interest, e.g. a volume including the hippocampus, is extracted and again a global registration of the corresponding volumes-of-interest in the training and diagnostic images is made. Good results are achieved as follows: 1. A global and local full brain registration of the training and diagnostic images—actually whole brain volumes, 2. Extract the VOIs in the training and diagnostic images, 3. Repeat the global and local registration between the VOIs. Based on these registered volumes-of-interest a segmentation proper stage 32 is applied to the more refined details in the volume-of-interest, e.g. the anatomical details of the hippocampus. The segmentation proper includes an active deformable surface method that combines a data term represented by a Chan-Vese term plus a prior term in terms of image moments. The role of this method is to improve on the initial segmentation provided by the initialization process; the latter deforms the annotated sub-structures, via the registration method, to the regions close to that of their correct positions in the diagnostic magnetic resonance image of the brain. For example, the full brain registration is realized by the Elastix image registration software between the training magnetic resonance image that includes the annotation set obtained from atlases ($T_2$-weighted 7 T MRI brain volume) and a r target brain volume ($T_2$-weighted 3 T MRI brain volume) of the diagnostic magnetic resonance image. This registration is done in two steps: (i) global affine transformation, and (ii) local registration based on B-splines. The VOI extraction is such that it uses a binary mask (all sub-structures with the intensity of 255) and its envelope plus a region of "security" made up by M voxels in each cardinal direction. The VOIs for the 7 T and 3 T volumes are registered between themselves by applying again the Elastix method.

Thus, the accurate annotations in that each hippocampus sub-structure has a label and constant intensity (grey level) values and segmented anatomical details in the atlas of training magnetic resonance images is accurately transferred into a segmentation and annotation in the output diagnostic image 40 from the segmentation segment 30.

As to the atlas 50 of training magnetic resonance images, these are generated from a set of e.g. a dozen or more, ultra-high field magnetic resonance images. For these training magnetic resonance images, at ultra-high, e.g. 7 T or more, main magnetic field strength magnetic resonance signals are acquired 40 from several volunteers. From these magnetic resonance signals the training magnetic resonance images are reconstructed 61 and annotated 62 by a group of radiological experts. This leads to an atlas 70 of annotated high-diagnostic quality (contrast resolution) training magnetic resonance images. These training images include an accurate and reliable segmentation and annotation of fine anatomical details such as details of the anatomical structure of the hippocampus. For example, the training data is made up of ten annotated 7 T MRI brains. Each brain is from another volunteer. Using the volumes of each substructure a set of parameters corresponding to their geometrical moments; these parameters are the training data.

Figure 2:
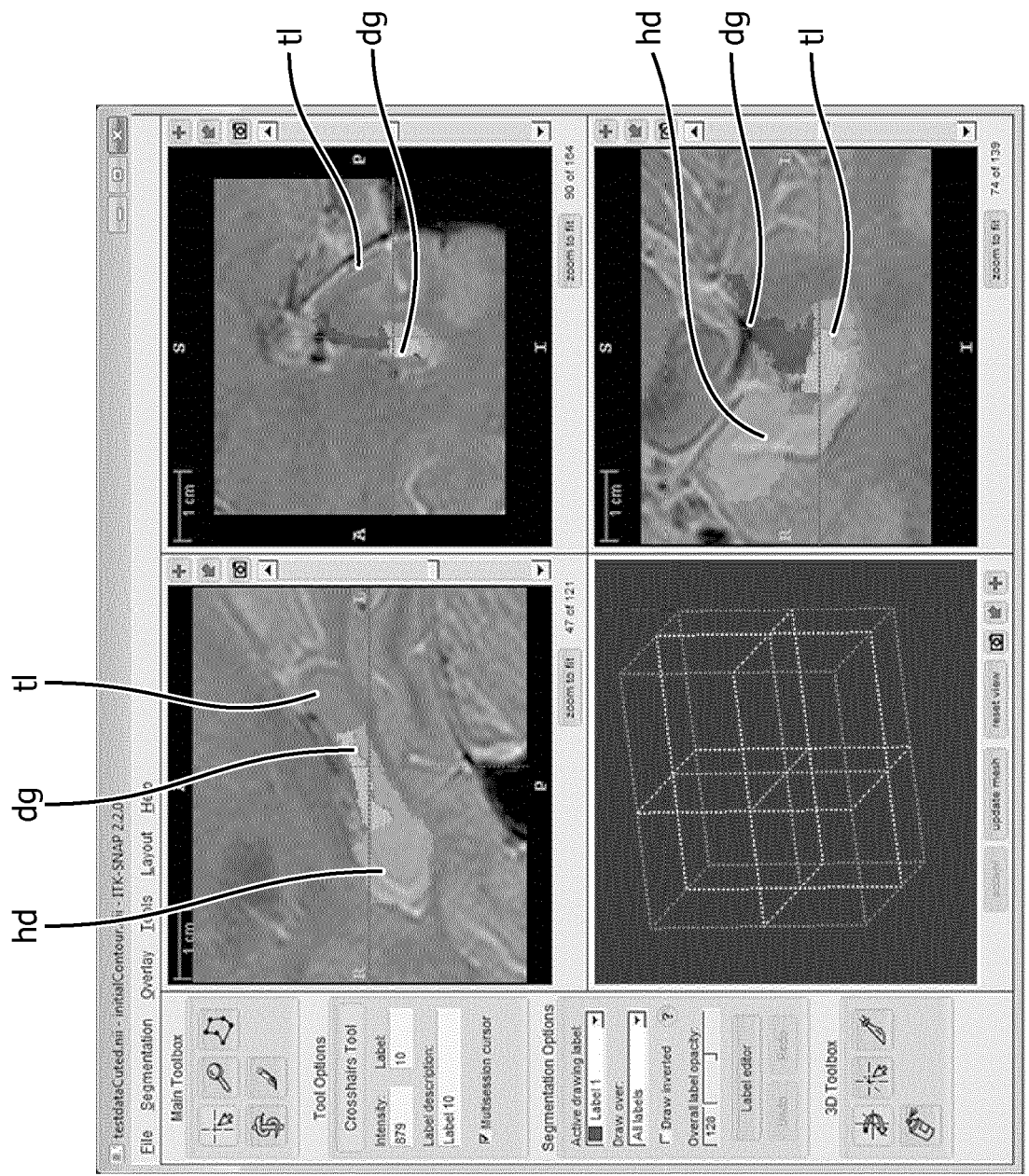
FIG. 2 shows an example of the segmentation of hippocampus sub-structures, left side of the brain hemisphere. Three views that show the segmentation labels superimposed on the VOI of the 3 T brain MRI.

FIG. 2 shows an example of the segmentation of hippocampus sub-structures, left side of the brain hemisphere. Three views that show the segmentation labels superimposed on the VOI of the 3 T brain MRI. The hippocampus head is annotated 'hd, the tail as 't1 and the dentate gyrus 'dg'.

Figure 3:
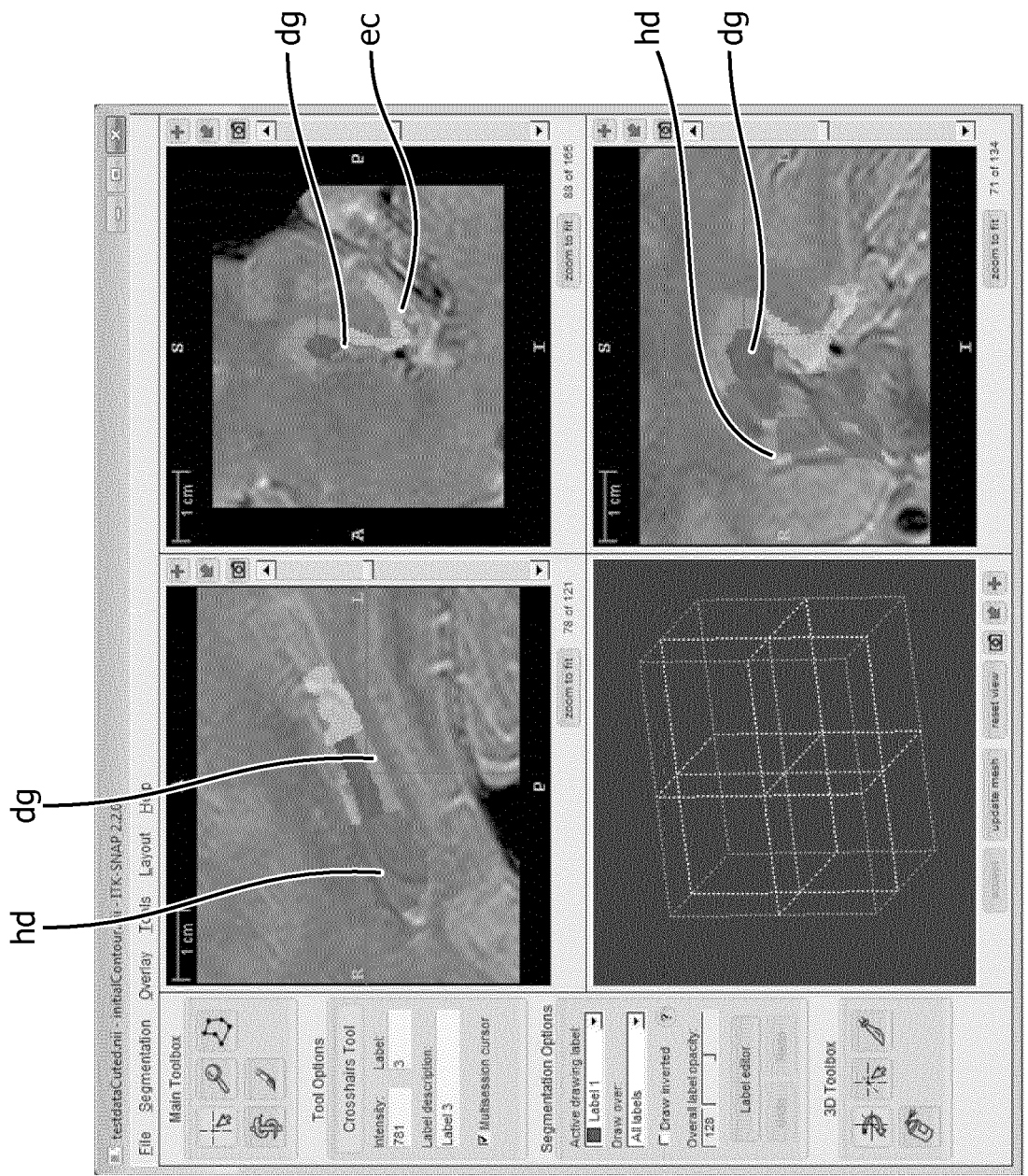
FIG. 3 shows an example of the segmentation of hippocampus sub-structures, right side of the brain hemisphere. Three views that show the segmentation labels in different colours superimposed on the VOI of the 3 T brain MRI.

FIG. 3 shows an example of the segmentation of hippocampus sub-structures, right side of the brain hemisphere. Three views that show the segmentation labels in different colours superimposed on the VOI of the 3 T brain MRI. The hippocampus head is annotated 'hd, the tail as 't1 and the dentate gyrus 'dg' and the entorhinal cortex as 'ec'.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A magnetic resonance imaging protocol comprising:
an acquisition segment configured to control a parallel imaging acquisition sequence to acquire magnetic resonance signals at a lower main magnetic field strength, wherein the parallel imaging acquisition sequence is a 3D multi-echo single-shot turbo spin echo sequence, wherein:
a repetition time TR is in the range of 2000-3000 ms,
an echo time is in the range of 200-250 ms,
an echo train length has 150-170 echoes and echo spacing per shot in the range of 4.4/720 ms to 5.2/880 ms, and
wherein the acquisition sequence performs a half-Fourier scanning of k-space in the phase-encode direction with a half-Fourier factor in the range of 0.60 to 0.73, wherein the parallel imaging acquisition sequence has a sampling reduction factor in the range of 1.3-1.5 in a first phase-encoding direction and a sampling reduction factor in the range of 1.8-2.2 in a second phase-encoding direction,
a reconstruction segment configured to control reconstruction of a diagnostic magnetic resonance image from the magnetic resonance signals at the lower main magnetic field strength and
a segmentation segment configured to control segmentation of a predetermined image detail of the diagnostic magnetic resonance image,
wherein the acquisition sequence has a set of imaging parameters that cause the image quality of the diagnostic magnetic resonance to be similar to the image quality of magnetic resonance training images acquired at main magnetic field of a higher main magnetic field strength and
wherein the segmentation segment comprises:
an initialization portion which controls access to a set of magnetic resonance training images, and
registration of the diagnostic magnetic resonance image to one or more of the magnetic resonance training images,
the one or more magnetic resonance training images including an image detail corresponding to the predetermined image detail in the diagnostic magnetic resonance image and the segmentation segment comprises a segmentation proper applied to the diagnostic image to segment the predetermined detail from the registered diagnostic magnetic resonance images.

2. The magnetic resonance imaging protocol of claim 1, wherein the repetition time TR is substantially 2200 ms or 2400 ms.

3. The magnetic resonance imaging protocol of claim 1, wherein the echo time is substantially 211 ms or 226 ms.

4. The magnetic resonance imaging protocol of claim 1, wherein the echo spacing per shot is substantially 4.8/804 ms.

5. The magnetic resonance imaging protocol of claim 1, wherein the half-Fourier factor is substantially 0.675.

6. A magnetic resonance imaging method comprising:
with a 3D multi-echo single-shot turbo spin echo parallel imaging sequence, acquiring magnetic resonance signals at a lower magnetic field strength with a set of imaging parameters that cause an image quality of a diagnostic magnetic resonance image to be similar to an image quality of magnetic resonance training images acquired at a higher main magnetic field strength, wherein:
  a repetition time TR of the parallel imaging sequence is in the range of 2000-3000 ms,
  an echo time is in the range of 200-250 ms,
  an echo train length has 150-170 echoes, and echo spacing per shot is in the range of 4.4/720 ms to 5.2/880 ms, and
  wherein the parallel imaging acquisition sequence has a sampling reduction factor in a range of 1.3-1.5 in a first phase-encoding direction and a sampling reduction factor in a range of 1.8-2.2 in a second phase-encoding direction;
reconstructing the diagnostic magnetic image from the magnetic resonance signals at the lower main magnetic field strength;
segmenting a predetermined image detail of the diagnostic magnetic resonance image;
accessing a set of magnetic resonance training images;
registering the diagnostic magnetic resonance image to one or more of the magnetic resonance training images;
wherein the one or more magnetic resonance training images include an image detail corresponding to the predetermined image detail of the diagnostic magnetic resonance image.

7. The magnetic resonance imaging method of claim 6, wherein the repetition time TR is substantially 2200 ms-2400 ms.

8. The magnetic resonance imaging method of claim 6, wherein the echo time is substantially 211 ms-226 ms.

9. The magnetic resonance imaging method of claim 6, wherein the echo spacing per shot is substantially 4.8/804 ms.

10. The magnetic resonance imaging method of claim 6, wherein the parallel imaging acquisition sequence performs half-Fourier scanning of k-space with a half-Fourier factor of substantially 0.675.

11. A magnetic resonance imaging apparatus comprising:
a training image atlas which stores a plurality of training images generated at a higher magnetic field strength, the training images being annotated to indicate one or more predetermined image details;
one or more processors configured to:
  control a magnetic resonance imaging system to perform a parallel imaging acquisition sequence at a lower magnetic field strength to acquire magnetic resonance signals, the parallel imaging acquisition sequence having a sampling reduction factor in the range of 1.3-1.5 in a first phase-encoding direction and a sampling reduction factor in the range of 1.8-2.2 in a second phase-encoding direction,
  reconstruct the magnetic resonance signals acquired at the lower magnetic field strength into a diagnostic magnetic resonance image,
  segment a predetermined image detail of the diagnostic magnetic resonance image,
  registering the diagnostic magnetic resonance image to one or more of the magnetic resonance training images,
  register the segmented image detail of the diagnostic magnetic resonance image and the corresponding segmented detail of one or more of the magnetic resonance training images,
  control a display device to display the diagnostic image with the segmented detail registered to the corresponding portion of the one or more training images.

12. The magnetic resonance imaging apparatus of claim 11, wherein the parallel imaging acquisition sequence is a 3D multi-echo single-shot turbo spin echo sequence, wherein:
  a repetition time TR of the parallel imaging sequence is in the range of 2000-3000 ms,
  an echo time is in the range of 200-250 ms,
  an echo train length has 150-170 echoes,
  an echo spacing per shot is in the range of 4.4/720 ms to 5.2/880 ms, and
  wherein the parallel imaging acquisition sequence performs a half-Fourier scanning of k-space with a half-Fourier factor in the range of 0.60 to 0.70.

13. The magnetic resonance imaging apparatus of claim 11, wherein the repetition time TR is 220 ms-2400 ms.

14. The magnetic resonance imaging apparatus of claim 11, wherein the echo time is 211 ms-226 ms.

15. The magnetic resonance imaging apparatus of claim 11, wherein the echo spacing per shot is substantially 4.8/804 ms.

16. The magnetic resonance imaging apparatus of claim 11, wherein the half-Fourier factor is substantially 0.675.

* * * * *